United States Patent
Wright et al.

(10) Patent No.: US 10,287,237 B1
(45) Date of Patent: May 14, 2019

(54) POLYMERIC MATERIALS MADE FROM VANILLIN

(71) Applicant: The United States of America, as represented by the Secretary of the Navy, Washington, DC (US)

(72) Inventors: Michael E. Wright, Ridgecrest, CA (US); Benjamin G. Harvey, Ridgecrest, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/782,223

(22) Filed: Oct. 12, 2017

Related U.S. Application Data

(62) Division of application No. 15/141,930, filed on Apr. 29, 2016, now Pat. No. 9,815,775, which is a division of application No. 13/678,864, filed on Nov. 16, 2012, now Pat. No. 9,353,219.

(60) Provisional application No. 61/562,118, filed on Nov. 21, 2011, provisional application No. 61/562,242, filed on Nov. 21, 2011.

(51) Int. Cl.
| | |
|---|---|
| *C07C 253/04* | (2006.01) |
| *C07C 37/00* | (2006.01) |
| *C07C 37/16* | (2006.01) |
| *C12P 13/00* | (2006.01) |
| *C08G 65/38* | (2006.01) |
| *D06M 13/345* | (2006.01) |
| *D06M 101/40* | (2006.01) |

(52) U.S. Cl.
CPC .......... *C07C 253/04* (2013.01); *C07C 37/002* (2013.01); *C07C 37/003* (2013.01); *C07C 37/16* (2013.01); *C08G 65/38* (2013.01); *C12P 13/002* (2013.01); *D06M 13/345* (2013.01); *D06M 2101/40* (2013.01)

(58) Field of Classification Search
CPC ..... C07C 253/04; C07C 37/16; C07C 37/002; C07C 37/003
See application file for complete search history.

(56) References Cited

U.S. PATENT DOCUMENTS 5,051,184 A 9/1991 Taylor

OTHER PUBLICATIONS

Zaragoza Dorwald, Side Reactions in Organic Synthesis, 2005, WILEY-VCH Verlag GmbH & Co. KGaA, Weinheim, Preface. p. IX . (Year: 2005).*
McMurry, Chemical Reviews, Carbonyl-Coupling Reactions Using Low-Valent Titanium, 1989, 89, pp. 1513-1524. (Year: 1989).*
Harvey et al, Polymer Preprints, Synthesis and Properties of Renewable High Temperature Cyanate Ester Thermosets Derived from Vanillin, 2011, 52(1), pp. 1-3. (Year: 2011).*
Harvey et al (Polymer Preprints, Synthesis & Properties of Renewable High Temperature Cyanate Ester Thermosets Derived from Vanillin, 2011, pp. 1-2,Jun. 8, 2015.
St. Pfau (Helvetica Chimica Acta,Catalytic hydrogenation of vanillin. Vanillylcreosol, 1939, 22, pp. 550-554).
Synthesis of 3,5-dihydroxybenzoic acid (y-resorcylic acid) from benzoic acid see: Suter, C. M.; Weston, A. W. J. Am. Chem. Soc. 1939, 61, 232.
Y-resorcylic acid esters were prepared by modifying the procedure of Suter, C. M.; Weston, A. W. J. Am. Chem. Soc.1939, 61, 531.
Chemistry and Technology of Cyanate Esters, Hamerton, I. Ed.; Chapman and Hall: Glassgow, 1994.
Hamerton et al., Polymer 42 (2201) 2307-2319.
PG alkylation in 20% yield: Steidl et al.. J. Mater. Chem. 2009, 19.
Caplus Chem Abstracts Service Columbus OH, US; Database ace No. 1973:536751, Abstract of Kurth et al. Chem Berichte (1973), 106(8), 2419-26.
Wright et al., Macromolecules, vol. 40, No. 11, 2007.
Hou et al., Tetrahedron 63 (2007) 10801-10808 &Chaplin et al., Macromolecules, vol. 27, 4927-4935, 1994.
Fujisawa et al, (anticancer research) Kin. Radical Scaven'g Activity & Cyto. of 2-methoxy & 2-t-butyl-subst. phenols & their dimers, 2004, 24, 3019-3026.
Yusuf et al, (Med. J. of Chem., Synthesis via phenolic oxidative coupling using crude peroxidase from *Brassica juncea* 2014, 3(6) 1100-1110.

* cited by examiner

*Primary Examiner* — Paul A Zucker
(74) *Attorney, Agent, or Firm* — Charlene A. Haley

(57) ABSTRACT

A method for converting vanillin to bis(cyanate) ester monomers, comprising treating vanillin with a reductive coupling agent to form at least one olefin. The olefin or olefins are treated with hydrogen and a metal catalyst to hydrogenate said olefin. The hydrogenated olefin or olefins are treated with at least one cyanogen halide and a base in an organic solvent to afford at least one olefin monomer. The olefin monomer or monomers are purified by recrystallization or precipitation from an organic solvent.

2 Claims, 5 Drawing Sheets

POLYMERIC MATERIALS MADE FROM VANILLIN

CROSS-REFERENCE TO RELATED APPLICATIONS

This is a divisional patent application, claiming benefit of, parent non-provisional application Ser. No. 15/141,930 filed on Apr. 29, 2016, which is now U.S. Pat. No. 9,815,775, claiming benefit of, parent non-provisional application Ser. No. 13/678,864 filed on Nov. 16, 2012, which is now U.S. Pat. No. 9,353,219, claiming the benefit of, parent provisional application Ser. No. 61/562,118 filed on Nov. 21, 2011, which is now expired, and this application is a continuation-in-part and claims benefit of parent provisional application Ser. No. 61/562,242 filed on Nov. 21, 2011, which is now expired, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to vanillin being a precursor to high performance resins and related polymer systems.

Figure 1:
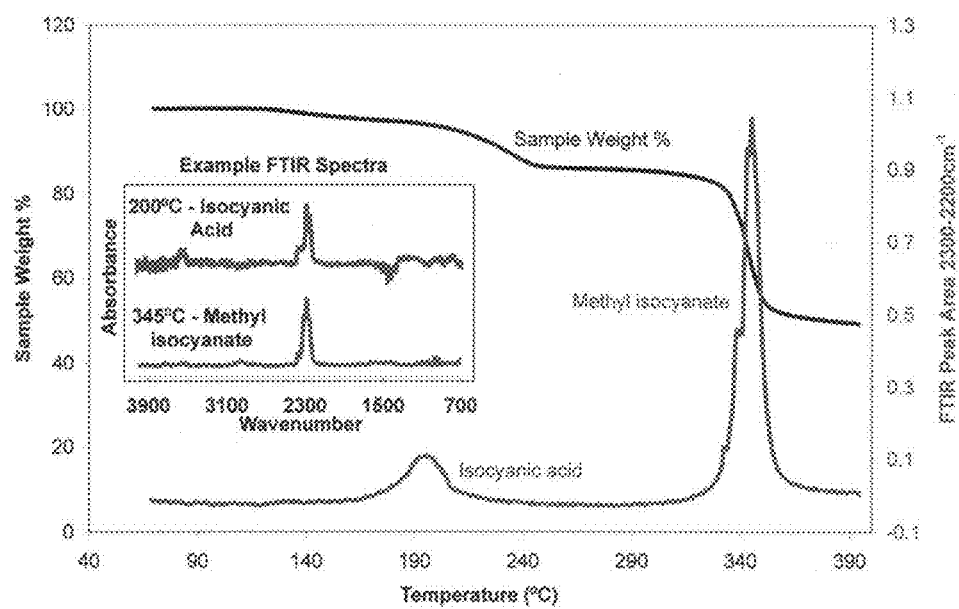
FIG. 1 is a graph that utilized TGA/FTIR spectroscopy to analyze the thermal cure of monomer, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

The invention generally relates to the naturally occurring organic molecule vanillin being a starting material for preparation of high performance resins and related polymer systems.

The NAVY and DoD need a supply of composite resins that are based on US sources and will be fully sustainable and renewable. The latter meaning the chemical feedstock is independent of petroleum and related sources. The NAVY also has a continuing need for new high performance (HP) composite resins with low water uptake thus providing a distinctive advantage to NAVY weapon, aircraft, and sea platforms. This work is particularly important for the NAVY since it addresses and solves a recognized performance gap and delivers a composite resin derived from a US made feedstock, vanillin, which is fully sustainable and renewable.

By developing this class of high performance resins based on vanillin we have shown the ability to tailor and control the glass-transition temperature ($T_g$) of the cured resins as well as the water uptake. Examples have been made that show vanillin is a powerful precursor to high performance and related polymer systems. In addition, these monomers can be made from sustainable and renewable bioaromatic feedstocks based on waste lignin from cellulosic biofuel and paper mill industries.

Few examples exist for making high performance composite resins from renewable resources (i.e. bioaromatics) in an efficient and cost effective manner. Vanillin is readily obtained from biomass waste including lignin.

This work addresses the synthetic challenges of preparing a variety of bis(cyanate) esters and related polymers that include, but are not limited to, polyesters, polyamides, polycarbonates, epoxies, and acrylates made from vanillin and functionalized precursors thereof. A goal of the embodiments of the invention is using a minimum number of chemical steps to transform the readily available biofeedstock vanillin into cyanate ester monomers that will ultimately lead to new and useful high performance composite resins.

Several new bis(cyanate) ester monomers were prepared based on the biofeedstock of vanillin. Oxidative coupling of 4-methyl-2-methoxyphenol, a reduced form of vanillin, afforded 5,5'-dimethyl-3,3'-dimethoxy-2,2'-bisphenol (Ranadive, A. S. Dev. Food Sci. 1994, 34, 517-577 and references cited therein.) and the latter was converted in 85% yield to the corresponding bis(cyanate) ester 2 by treatment with cyanogen bromide in the presence of triethyl amine. Reductive coupling of vanillin with a low valent titanium catalyst afforded E-1,2-bis(4-hydroxy-3-methoxyphenyl) ethene (5) in modest yield and the latter was readily converted to the saturated derivative, 1,2-bis(4-hydroxy-3-methoxyphenyl)ethane (6) in high yield (91%). Conversion to the bis(cyanate) ester derivatives 7 and 8 proceeded smoothly as well.

Vanillin is a naturally occurring and unique aromatic molecule. The pleasing taste and aroma of vanillin has made it a highly sought after chemical for centuries. One current method of production involves isolation from the seed pods of the orchid vanillin planifola. Vanillin represents only ~2% of the dry weight of the seed pods. Vanillin is chemically bound in the seeds as the β-D-glycoside and after a drying and aging period, the pure vanillin is released and isolated. Of the ~6000 tons of vanillin used per year, this isolation process from plants accounts for only ~0.2% of the worlds consumption:

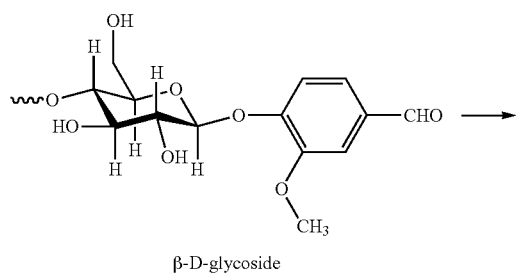

β-D-glycoside

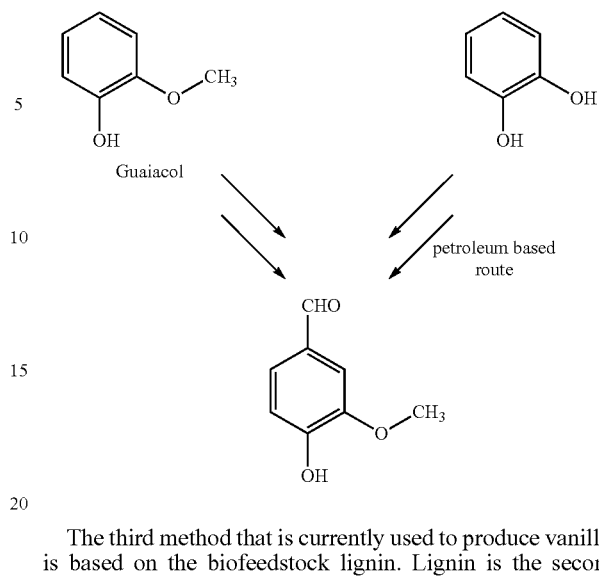

Guaiacol petroleum based route

CHO (vanillin structure)

The third method that is currently used to produce vanillin is based on the biofeedstock lignin. Lignin is the second most abundant organic polymer on the planet and can be purchased for less than 35 cents per pound. On a commercial scale, lignin can be depolymerized with base under oxidative-conditions to form vanillin in reasonable yield and in a cost effective manner.

A major drawback to isolation of vanillin from lignin is co-production of a considerable waste stream (~150 kg/1 kg vanillin). During the 1980's a lignin waste from one paper mill was the source for ~60% of the world's vanillin supply. More recently, lignin has become a useful by-product of cellulosic biofuel production. Lignin:

Vanillin

One significant route to synthetic (i.e. petroleum based) vanillin currently begins with guaiacol. Guaiacol can be isolated from the plant guaiacum: however, based on feedstock and isolation costs, the guaiacol currently prepared from petroleum derived catechol. Thus, this latter route from catechol represents a non-renewable source of vanillin utilizing "old carbon."

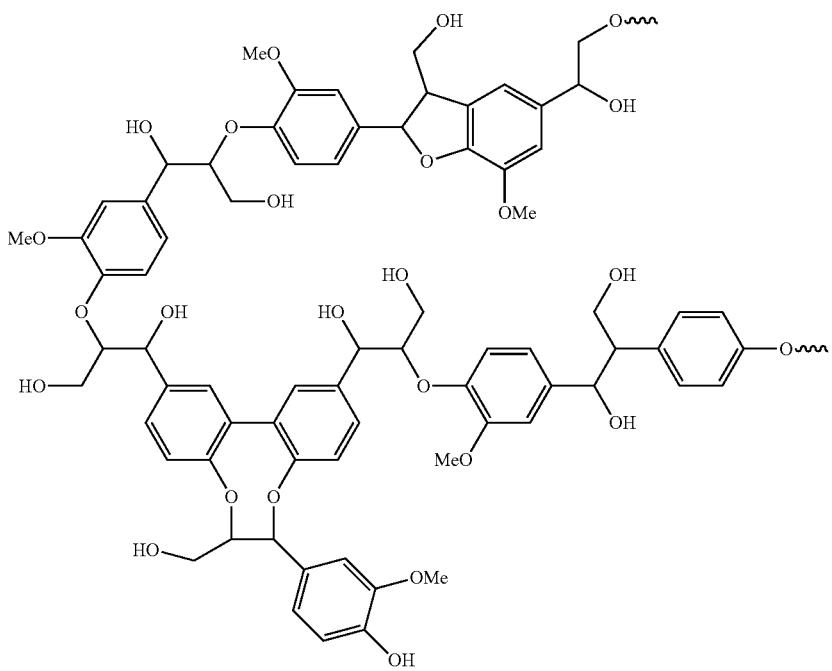

Partial Chemical Structure of Lignin is presently the most viable and cost effective source of renewable bioaromatics. As a consequence, new methods for both improving chemical efficiencies and also reducing the waste stream associated with isolating well defined monomeric/dimeric aromatic structures from lignin are under continual development.

High performance polymeric composite resins, whether a polyimide, cyanate ester, bismalimide, or similar, are based upon a network of aromatic structures. In this invention, we describe different methods of making vanillin based bisphenols followed by conversion of these compounds to make a series of new bis(cyanate) esters and present details on the thermal curing chemistry of vanillin-based bis(cyanate) esters as well as a look at the physical properties of the cured resins.

Synthesis of Bis-Phenols and Corresponding Cyanate Esters.

Figure 5:
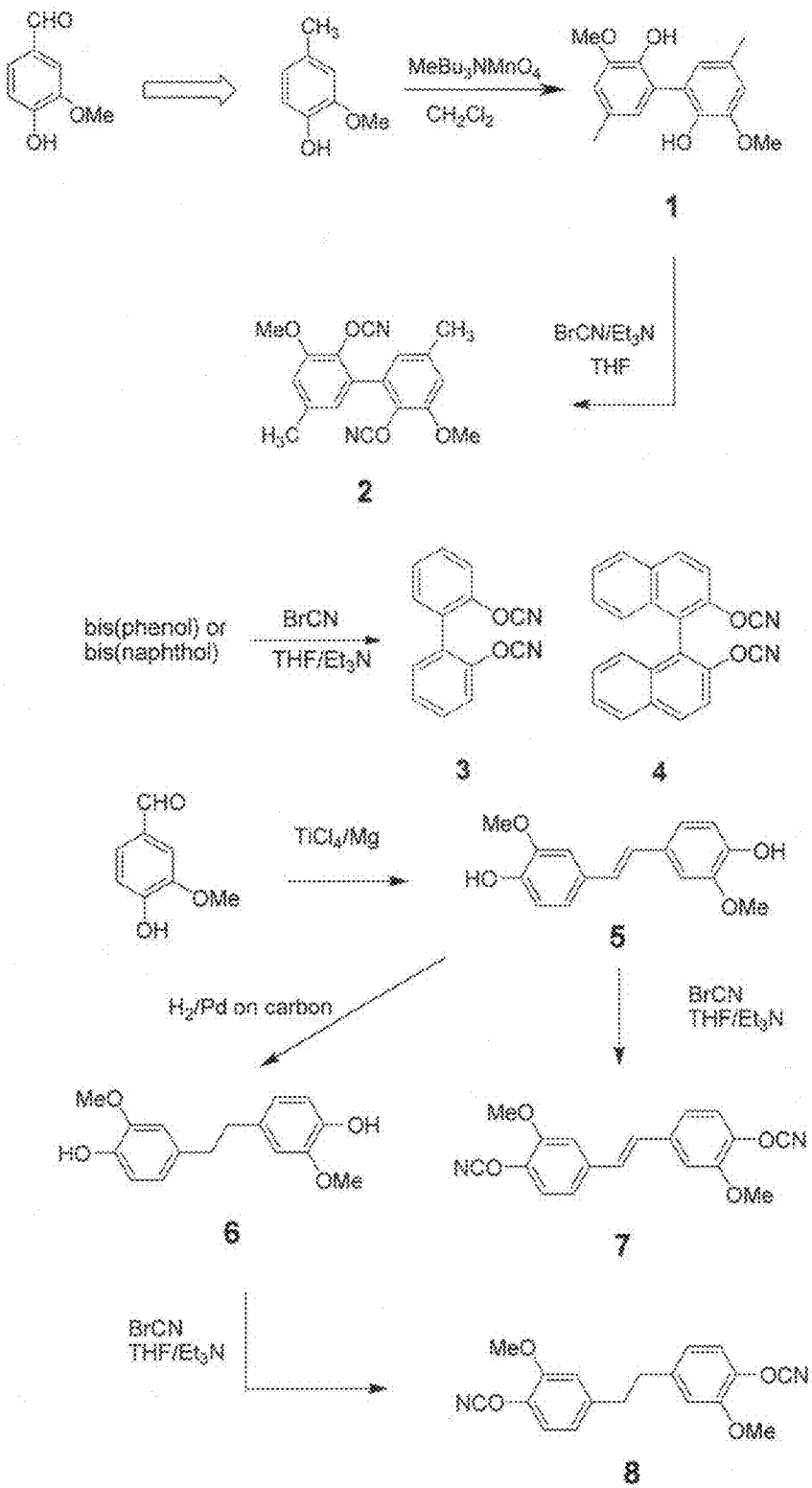
FIG. 5 is chemical reaction schemes, according to embodiments of the invention.

As a first attempt at making bis-cyanate esters from vanillin, we explored an oxidative coupling route. Reduction of the carboxaldehyde group in vanillin to yield 4-methyl-2-methoxyphenol in nearly quantitative yield has been demonstrated in the literature. Based on the lack of extraneous reactive functional groups, this molecule was chosen as a starting point. Although the literature abounds with reports on methods for coupling the phenolic rings of 4-methyl-2-methoxyphenol, a recent procedure detailed by Wang and coworkers uses the methylene chloride soluble permangate reagent, $MeBu_3NMnO_4$, to provide a clean conversion to the vanillin-biphenyl product (1) (FIG. 5). Although the crude yield of 1 is excellent, losses during purification resulted in comparable yields (~50%) to those reported in the literature. Suitably pure 1 was readily converted to the bis(cyanate) ester 2 in high yield (~85%) by treatment with cyanogen bromide in the presence of base:

Since there is little data in the literature concerning 2,2'-bis(cyanato)-1,1'-biphenyl derivatives, we invested the time to prepare model compounds 3 and 4:

Recently a chiral version of compound 4 was prepared although no cure chemistry of the cyanate ester was reported. As a result, the ability of monomer 4 to form a complete triazine network (i.e. fully cured resin) was not established.

As an alternate approach, we attempted to generate a bisphenol by means of a reductive coupling of the aldehyde group. Although vanillin has been reported as a substrate that is recalcitrant to reductive coupling by low valent metal species, the bis(phenolic)ethene (5) was isolated in good yield through a McMurry coupling without protection of the phenols (Scheme 3). Compound 5 was then hydrogenated over palladium on carbon to form the saturated bis(phenolic) ethane (6) in high yield (~90%). Conversion of 5 and 6 to their respective cyanate esters 7 and 8 was then carried out by treatment with cyanogen bromide in the presence of base.

Although in general, the bond lengths and angles in the solid state structures of 4, 7, and 8 are quite typical of cyanite esters, we sought to determine the extent to which intermolecular forces in these molecules impacted the melting points and ultimately the cure chemistry of these resins.

Efficient curing can only occur in the liquid phase, and a lower melting point is beneficial as it translates into a larger processing window for the material. Although 7, 4, and 8 have similar molecular weights and polarities, their melting points of 237, 205, and 190° C., respectively, are quite disparate. The strength of the intramolecular forces in these systems may also be qualitatively supported by the densities of the solids. Compounds 7, 4, and 8 have calculated densities of 1.399, 1.360, and 1.354 $g/cm^3$, respectively, and this trend directly corresponds to the decrease in observed melting point.

Bis(Vanillin Cyanate Ester) Curing Chemistry.

We first explored the cure chemistry of 2 which results in the following structure:

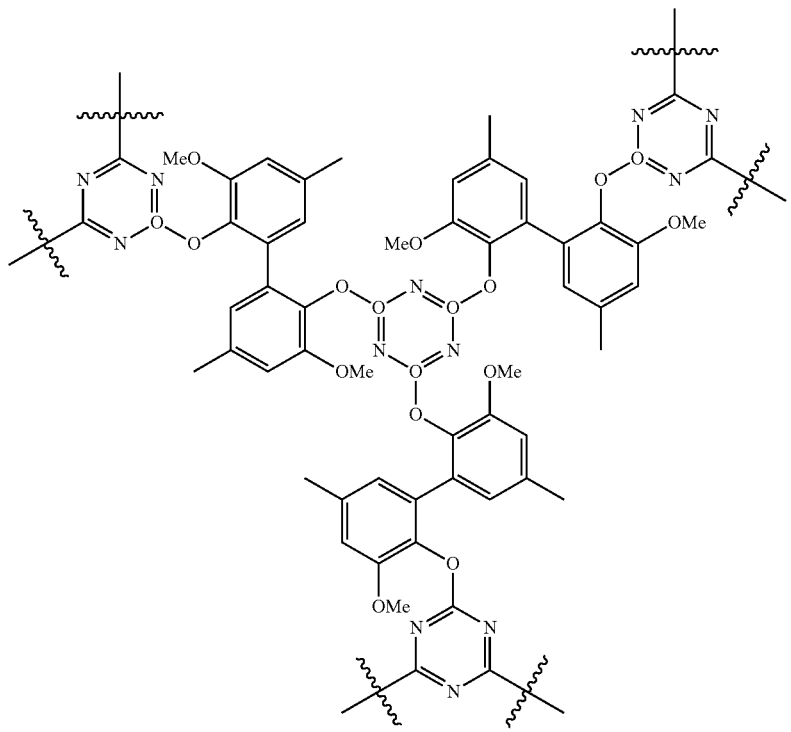

DSC analysis of 2 shows a somewhat broad melting point at 205° C., followed by an exotherm of 400 J/g (or 65 kJ/mol-equiv of cyanate ester) and a peak cure temperature near 270° C. The in-situ cure appears to start immediately upon melting, in line with the observations from sample molding. The exotherm also appears insufficient for full cure of the cyanate ester groups which should produce 100 kJ/mol-equiv of cyanate ester. Furthermore, the $T_g$ after in-situ cure of around 175° C. is 50-100° C. lower than what is expected based on full cure of bis(cyanate) esters with a similar cross-link density and architecture. After 24 h at 210° C., the as-molded sample shows a residual cure of around 12 kJ/mol-equiv cyanate ester with a $T_g$ near 195° C. The latter result indicates a more extensive, however, still incomplete cure.

Numerous attempts were made to degas and care the vanillin monomer 2 using both slow and rapid heating under both partial vacuum, and high vacuum with temperatures ranging from 100-200° C. In all cases some nitrogen atmosphere was applied to the samples under heating. For all attempts, the bis(cyanate) ester 2 is found to cure essentially concurrent with melting and this leads to samples which show incomplete consolidation. During the curing and heating process it appears there is a release of volatiles which is evidenced by bubbles within the cured samples. Thus for 2, we find that fabrication of void-free samples is quite difficult if not impossible.

In order to improve processing characteristics of bis (cyanate) ester monomer 2, we blended it in ~35 wt-% into Primaset® LECy. The latter is the bis(cyanate) ester prepared from Bisphenol E and exists as a super-cooled liquid at room temperature. After some stirring the bis(cyanate) ester monomer 2 is readily dissolved and forms a homogeneous mixture. The mixture is then degassed at 95° C. and cast into a silicone mold. This is followed by heating at 150° C. for 1 h and 210° C. for 24 h under flowing nitrogen to effect cure. A strong solid sample is formed, and although thin samples are homogeneous, bubbles can be seen in samples thicker than ~1 mm. Hence, even as a blend, significant volatiles are generated during the cure reaction and then became trapped within the fully cured sample.

Probing the thermal cure chemistry of monomer 2 by thermal gravimetric analysis (TGA) provided data that in addition to cure chemistry above 200° C., there is weight loss of ~15 wt-%. Further heating shows a leveling off of weight loss and not until over 300° C. do we serve the onset of a second and more dramatic weight loss from the cured resin. After the exotherm and weight loss ceases, the sample exhibits a final char-yield of ~50 wt-%. The 50% char yield corresponds to essentially turning monomer 2 into a graphite-like material with all the side groups removed from the biphenyl rings.

To further elucidate the reasons behind this early weight loss we utilized TGA/FTIR spectroscopy to analyze the thermal cure of monomer 2 as see in FIG. 1.

It is apparent during the heating/curing of monomer 2 that isocyanic acid is evolved at the melting point/cure point (~200° C.) of the resin. This accounts for the initial weight loss and explains the difficulty in obtaining void free resin bars:

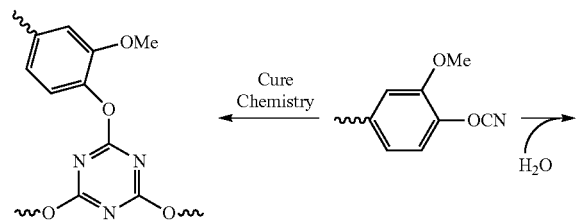

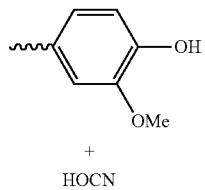

Figure 2:
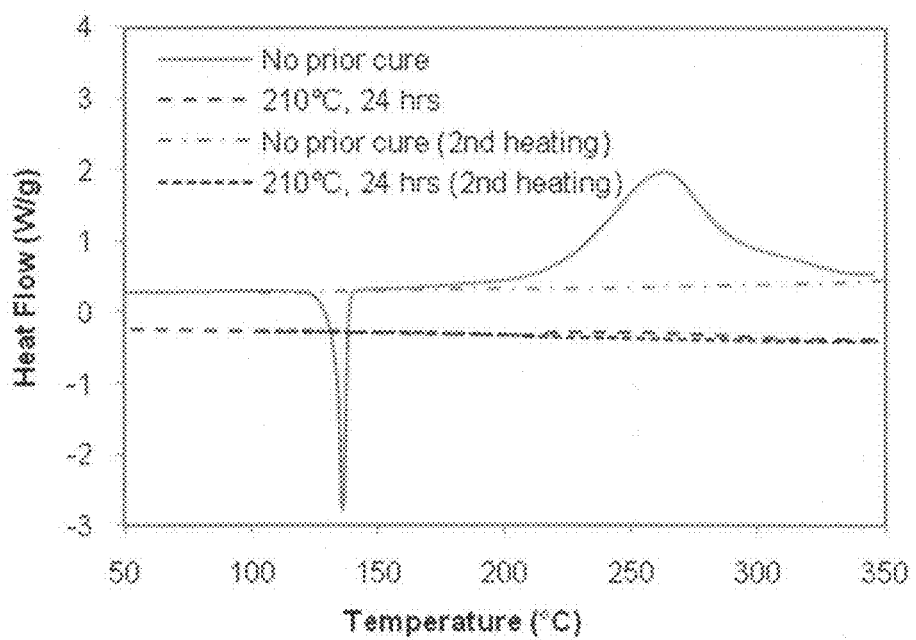
FIG. 2 is a graph that shows a DSC analysis for the thermal cure of the biphenyl monomer 3, according to embodiments of the invention.

DSC analysis for the thermal cure of the biphenyl monomer 3 is shown in FIG. 2, for the resin before and after in-situ cure, as well as before and after residual cure for samples molded at 210° C. for 24 h. The biphenyl cyanate ester 3 has a distinct melting point at 135° C., then exhibits a typical exotherm for cyanate esters with a peak temperature around 260° C. and an enthalpy of cyclotrimerization near the expected value of 100 kJ/mol-equiv cyanate ester. After 24 h at 210° C. the molded sample shows only a residual cure of ~6 kJ/mol-equiv cyanate ester. Since there is no guarantee that 100% conversion is achieved even after residual cure, the DSC data is consistent with a conversion of less than ~94% for the as-molded sample. The observed glass transition temperatures are around 210° C. for all cured samples. FT-IR analysis of the as-molded biphenyl cyanate ester clearly shows disappearance of the monomer and appearance of strong cyanate peaks with conversion estimated at 80-95%.

An analogous DSC analysis of the binaphthyl monomer 4 indicates a reduced enthalpy of cure of 70 kJ/mol-equiv cyanate ester, a peak cure temperature of only 210° C., and a somewhat larger residual cure after exposure to 210° C. for 24 h (5 kJ/mol-equiv cyanate ester). For this monomer we observe a glass transition temperature of around 210° C. for in-situ and as-molded cure and 230° C. after residual cure. Analysis of FT-IR spectroscopic data of the as-molded binaphthyl cyanate ester resin indicate a lower degree of conversion (45-75%) compared to the biphenyl monomer 3.

Taken together, the DSC and FT-IR data suggest that less than complete cure is achieved for as-molded biphenyl and binapthyl bis(cyanate) ester resins. Based on previously reported data for bis(cyanate) esters, including those containing napthyl groups, an estimate for the expected glass transition temperatures would be 0° C. for the uncured monomer and 300° C. for a fully cured resin. By applying the diBenedetto equation as a method to accurately predict $T_g$ values for intermediate conversions it can be concluded that our observed $T_g$ values of 210-230° C. correspond to conversions of 80-85%.[19] Thus it seems more likely, for both the biphenyl and binaphthyl monomer systems, that the FT-IR estimates for conversion are approximately correct and that full cure cannot be achieved even when samples are subsequently heated to 350° C. in the DSC. Although the biphenyl bis(cyanate) ester exhibited an exotherm sufficient to account for complete in-situ cure of a DSC sample, the post-in-situ-cure $T_g$ is not consistent with complete network formation in which side reactions or formation of non-network structures may be present. The brittleness of the as-molded specimens is another indication that network formation is not complete for these biphenyl and binaphthyl systems.

The difficulty in forming thermoset network polymers with an expected glass transition temperature greater than ~300° C. for the biphenyl and binapthyl CEs may result from steric hindrance around the cyanate groups, as well as from the controlled nature of the tricyanate networks formed. In particular, once the $T_g$ of the cured network becomes higher than the cure temperature, any additional cyclotrimerization will require a favorable arrangement of multiple cyanate ester groups. Such arrangements seem especially unlikely for the cyanate esters under consideration. Such an effect would explain the prevalence of a $T_g$ of 210° C. in the as-molded samples.

DSC analysis of compound 7 shows a sharp melting transition at 237° C. and a large enthalpy of melting of 230 J/g along with a melt-triggered exotherm of 160 kJ/mol-equiv cyanate ester. Since this value is considerably larger than typically seen for curing of the cyanate ester groups, it is likely that additional chemical reaction(s) takes place concomitant with cyclotrimerization. After heating the sample and allowing the cure/reaction chemistry to finish, we observe no glass transition in the DSC curve. As expected, when a sample of 7 is loaded in to a silicon mold large enough to accommodate compaction and is then heated to 150° C. at 300 torr under a nitrogen purge, no consolidation of the sample is observed. Further heating of the sample to 210° C. under 15 psi of nitrogen also results in no visible consolidation of the sample. After 24 h at 210° C., the partly consolidated sample was removed from the mold and analyzed by FT-IR spectroscopy. The FT-IR data indicate a conversion of 50-70% based on the disappearance of the cyanate ester monomer band; however, the cyanate peaks in the spectrum were somewhat smaller than expected.

Figure 3:
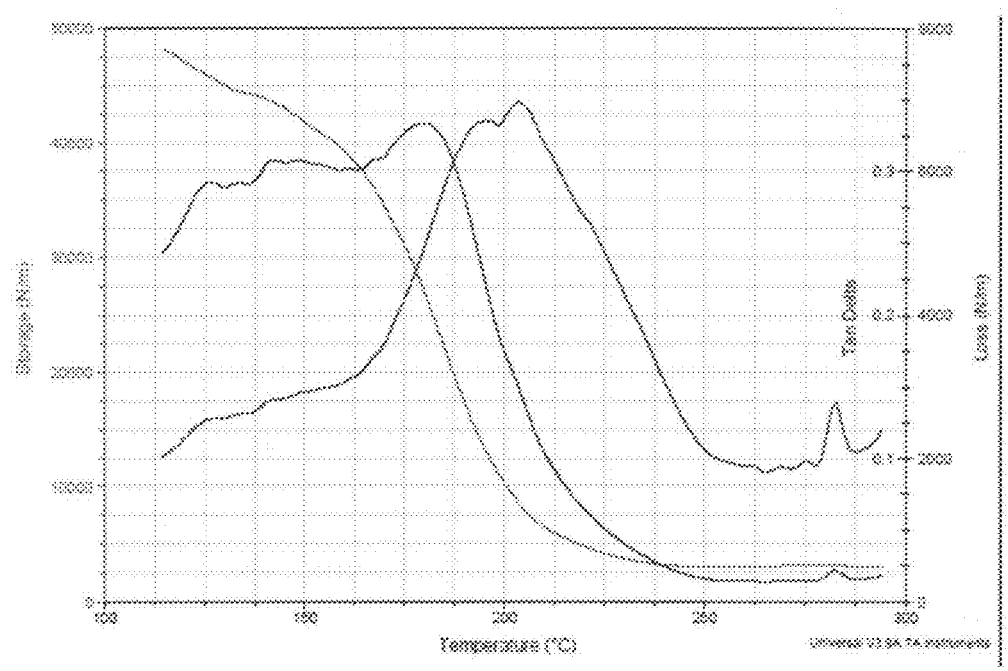
FIG. 3 is a graph showing TMA analysis after curing of vanillin bis(cyanate) ester monomer 8, according to embodiments of the invention.
Figure 4:
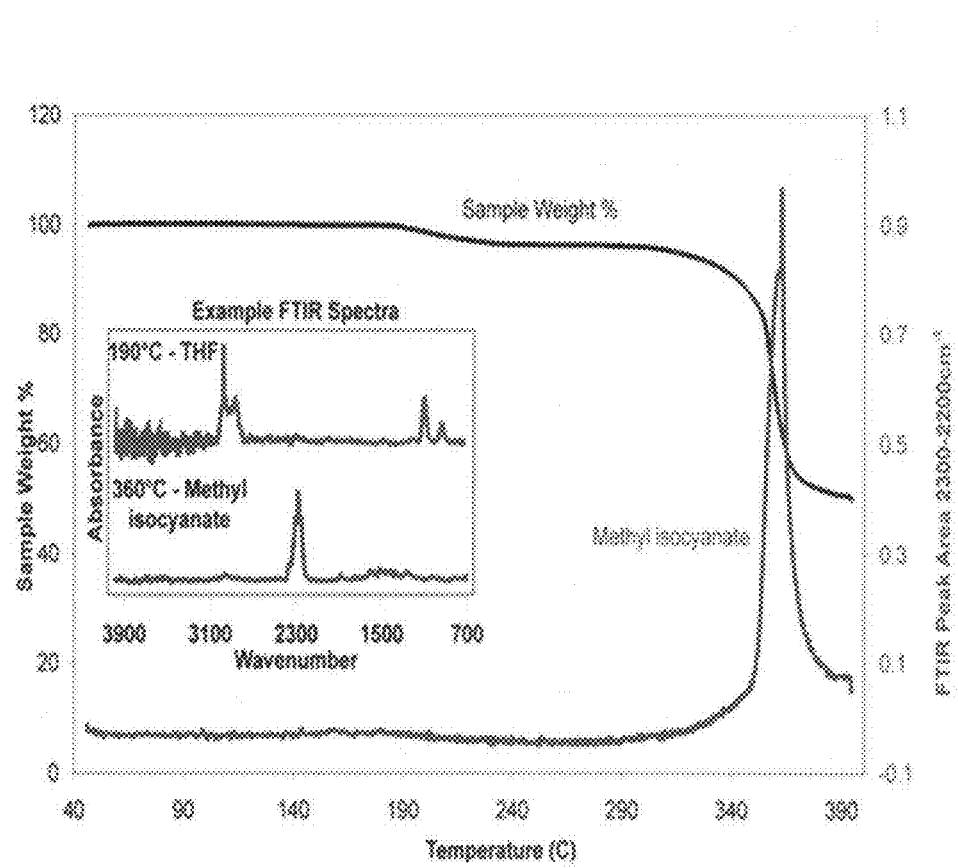
FIG. 4 is a graph showing FT-IR analysis indicating an extent of cure of approximately 98%, according to embodiments of the invention.

In contrast, samples of monomer 8 are found to consolidate and cure in a much more favorable manner. The DSC of monomer 8 was more typical of easily processed cyanate esters, although the observed melting point of 8 near 190° C. is higher than normal and results in a smaller, though still ample, process window, with a cure exotherm commencing shortly after the sample appears fully melted. The DSC measured cure exotherm of 92 kJ/mol-equiv cyanate ester is significantly greater than what we have see or compounds 2 and 4. When placed in a silicone mold and heated to 210° C. for 24 h, the sample was able to melt and compact over a period of a few minutes, well before the onset of significant cyclotrimerization, resulting in the formation of a void-free sample as cure proceeded. A DSC analysis of the as-molded sample reveals no detectable residual cure. Moreover, FT-IR analysis indicated an extent of cure of approximately 98%. The high quality of the sample allowed a more in-depth analysis of the thermomechanical properties of cured 8 via TMA, as shown in FIG. 4. The sample shows a peak in the loss modulus at 180° C. with a corresponding peak in tan-δ of 202° C. TMA analysis after curing of vanillin bis(cyanate) ester monomer 8 as seen in FIG. 3.

In this work we have demonstrated the successful synthesis of three new bis(cyanate) ester monomers based on the biofeedstock of vanillin. We find that direct connection of the vanillin to form a vanillin-biphenyl cyanate ester monomer affords a material that produces only partial cure, and because of a high melting point and the generation of volatiles, provides virtually no processing window. Model studies exploring the cure chemistry of unsubstituted biphenyl and binaphthyl bis(cyanate) esters reveal that difficulties in achieving full thermal cure can be problematic. By coupling the vanillin through the aldehyde group, we are able to form two new bis(cyanate) esters that in part allowed us to avoid the care difficulties associated with the bis(aryl) architecture. The unsaturated monomer 7 displays a very high melting point and we find that along with cyclotrimerization chemistry that other unproductive side-reactions occur. Based on the lack of consolidation and mechanical properties for the "cured" sample, it is apparent for 7 that a dense network is not formed. The thermal cure chemistry of monomer 8 proved very successful and defect free resin-bars can be prepared using standard processing techniques. The resin made from 8 by all accounts (spectroscopic and mechanical) appears to have under gone complete cure and displays excellent thermal stability at temperatures below the $T_g$ of 202° C.

General Experimental Methods for Selected Examples.

All manipulations of compounds and solvents were carried out using standard Schlenk techniques. $^1$H and $^{13}$C NMR measurements were performed using a Bruker AC 200 or Bruker 400 MHz instrument. $^1$H and $^{13}$C NMR chemical shifts are reported versus the deuterated solvent peak (Solvent: $^1$H, $^{13}$C: CDCl$_3$, δ 7.25 ppm, δ 77.0 ppm). Anhydrous DMF, inhibitor free anhydrous THF, inhibitor free anhydrous diethyl ether, vanillin, platinum oxide (PtO$_2$), titanium tetrachloride, 2-methoxy-4-methylphenol, methyltributylammonium chloride (aq. 70 wt-%), anhydrous triethyl amine, and cyanogen bromide were purchased from Aldrich Chemical Co. and used as received. For the McMurry-coupling chemistry, the THF was distilled from sodium/benzophenone under nitrogen prior to use. Elemental analyses were performed at Atlantic Microlab, Inc. Norcross, Ga. DSC measurements were performed using either a TA Instruments Q100 or Q200 differential scanning calorimeter under a N$_2$ purge of 30 cc/min and 50 cc/min, respectively.

Preparation of 3,3'-dimethoxy-5,5'-dimethyl-[1,1'-biphenyl]-2,2'-diol (1).

Bu$_3$MeNMnO$_4$ (10.9 g, 34.1 mmol) was dissolved in CH$_2$Cl$_2$(250 mL) placed in an ice bath and allowed to cool. Then 2-methoxy-4-methylphenol (9.95 g, 72.0 mmol) was added dropwise to the CH$_2$Cl$_2$ solution and allowed to react with stirring for 1 h at 0° C. under N$_2$. The reaction mixture was diluted with H$_2$(~200 mL) and the mixture stirred for an additional 30 min. The mixture was filtered through a glass-wool plug to remove the MnO$_2$ and the organic layer separated. The organic layer was washed with 0.1 M HCl (3×150 mL), brine (50 mL), and then dried over MgSO$_4$. Removal of the solvent under reduced pressure afforded 1 as a yellow powder (5.97 g, 60% yield). Purification of 1 was achieved using column chromatography on silica gel and elution with ethyl acetate/hexanes (1/4, v/v) to afford a 50% overall yield.

Preparation of 2,2'-dicyanato-3,3'-dimethoxy-5,5'-dimethyl-1,1'-biphenyl (2).

A THF (30 mL) solution containing 1 (0.971 g, 3.5 mmol) CNBr (1.032 g, 9.8 mmol) was placed in a dry ice and acetone bath at −40° C. Et$_3$N (0.738 g, 7.30 mmol) was added and the solution was allowed to stir at −40° C. for 2 h under N$_2$. The solution was diluted with ether (~150 mL) and washed with water (2×200 mL), brine (50 mL), and then dried over MgSO4. Removal of the solvent under reduced pressure afforded 2 as an off-white powder (1.06 g, 94%). Further purification can be achieved by recrystallization from acetonitrile (0.96 g, 85%). $^1$H NMR (CDCl$_3$) δ 6.91 (d, J=2 Hz, 2 H), 6.72 (d, J=2 Hz, 2 H), 4.00 (s, 3 H) 2.41 (s, 3 H); $^{13}$C NMR (CDCl$_3$) δ 150.1, 138.9, 137.8, 127.2, 123.1, 114.5, 110.2, 56.7, 21.7. Anal. Calcd for C$_{18}$H$_{16}$O$_4$N$_2$: C, 66.86; H, 4.97. Found: C, 65.77; H 5.09.

Preparation of 2,2'-bis(cyanato)-1,1'-biphenyl (3).

Using the procedure above monomer 3 was prepared in 65% yield: $^1$H NMR (CDCl$_3$) δ 7.64 (dd, J=8, 1.5 Hz, 2 H), 7.59 (pseudo dt, J=8, 2 Hz, 2 H), 7.45 (pseudo dt, J=8, 2 Hz, 2 H), 7.38 (dd, J=8, 2 Hz); $^{13}$C NMR (CDCl$_3$) δ 150.2 (ipso-OCN), 132.5, 131.1, 127.4, 124.2, 115.3, 108.4. Anal. Calcd for C$_{14}$H$_8$O$_2$N$_2$: C, 71.18: H, 3.42. Found: C, 71.28: H 3.46.

Preparation of 2,2'-bis(cyanato)-1,1'-binaphthyl (4).

Using the procedure above monomer 4 was prepared in 65% yield: $^1$H NMR (CDCl$_3$) δ 8.22 (d, J=9 Hz, 2 H), 8.05 (d, J=8 Hz, 2 H), 7.88 (d, J=9 Hz, 2 H), 7.60 (ddd, J=8, 7, 1 Hz, 2 H), 7.45 (ddd, J=8, 7, 1 Hz, 2 H), 7.17 (dd, J=8, 1 Hz, 2 H); $^{13}$C NMR matched that reported in the literature. Suitable crystals to the single-crystal molecular structure determination were grown from hot solution of acetonitrile.

Preparation of (E)-4,4'-(ethene-1,2-diyl)bis(2-methoxyphenol) (5).

A flask was charged with 2.35 g of Mg (96.7 mmol) and anhydrous THF (100 mL). The mixture was chilled to −78° C. and then TiCl$_4$ (10.6 mL, 96.5 mmol) was added dropwise through an addition funnel. The flask was allowed to slowly warm up to room temperature and the mixture transitioned to green slurry and finally a black solution. After stirring at room temperature for 30 min a THF (50 mL) solution of vanillin (7.01 g, 46.1 mmol) was added dropwise. The reaction was mildly exothermic and resulted in a dark brown mixture. The mixture was heated at reflux for 16 h and was then cooled to room temperature. The solvent was removed under reduced pressure and the residue treated with 100 mL of 2 M HCl to yield a dark solution with pale brown suspended solid. The mixture was filtered on a medium frit and the isolated solid was washed with water (3×50 mL) and chilled ethanol (3×25 mL 0° C.). The solid was dried in a vacuum oven (~10 Torr, 45° C.) overnight to yield 2.91 g of pale brown solid (46% yield). The purity of the crude product (>98%) was suitable for later synthetic procedures, but the material can be further purified by dissolution in THF followed by precipitation with hexane. X-ray quality crystals were grown by slow evaporation of a concentrated THF solution. $^1$H NMR (DMSO-d$_6$); δ 9.07 (s, 2 H, Ph-OH), 7.13 (d, 2 H, J=2 Hz), 6.94 (s, 2 H), 6.93 (dd, 2 H, J=8, 2 Hz), 6.73 (d, 2 H, J=8 Hz), 3.81 (s, 6 H, (OMe); $^{13}$C NMR (DMSO-d$_6$): δ 147.8, 146.2, 129.2, 125.8, 119.5, 115.6, 99.6, 55.6.

Preparation of 4,4'-(ethane-1,2-diyl)bis(2-methoxyphenol) (6).

A Parr reaction vessel was charged with (E)-4,4'-ethene-1,2-diyl)bis(2-methoxyphenol) (2.85 g, 10.5 mmol), THF (50 mL), PtO$_2$ (70 mg), and then placed under hydrogen (30 psig) and allowed to react at ambient temperature for 16 h with continuous agitation. The mixture was filtered through glass wool to remove platinum and the THF was removed under reduced pressure. The solid was washed with hexanes (2×30 mL) and dried under reduced pressure to afford 2.62 g of light brown solid (91% yield). $^1$H NMR (DMSO-d$_6$) δ 8.66 (s, 2H, Ph-OH), 6.73 (s, 2 H), 6.65-6.53 (m,4 H), 3.70 (s, 6 H, OMe), 2.70 (s, 4 H, CH$_2$): $^{13}$C NMR (DMSO-d$_6$): δ 147.7, 144.9, 133.1, 120.9, 115.6, 113.1, 56.0 (OMe), 37.6 (CH$_2$).

Preparation of (E)-1,2-bis(4-cyanato-3-methoxyphenyl) ethene (7).

A round bottom flask was charged with 0.70 g (2.6 mmol) of (E)-4,4'-(ethene-1,2-diyl)bis(2-methoxyphenol), THF (30 mL), and CNBr (0.69 g, 6.5 mmol). The mixture was chilled to −78° C. and triethylamine (0.75 mL) was then added dropwise by syringe. The pale brown solution was allowed to warm to room temperature and a tan solid precipitated. After stirring at ambient temperature for 20 min, the slurry was filtered and solid collected on a medium glass-frit. The solid washed with water (3×20 mL) and air dried to yield 640 mg (77%) of the crude product. Recrystallization from hot THF yielded 530 mg of off-white needles. Crystals suitable for an X-ray diffraction study were grown by slowly cooling a concentrated acetonitrile solution. $^1$H NMR (DMF-d$_7$) δ (d, 2H, J=2 Hz), 7.60 (d, 2 H, J=9 Hz), 7.50 (s, 2 H, —CH=CH—), 7.35 (dd, 2 H, J=9, 2 Hz), 4.07 (s, 3 H, OMe).

Preparation of 1,2-bis(4-cyanato-3-methoxyphenyl)ethane (8).

A round bottom flask was charged with 1.05 (3.8 mmol) of 4,4'-(ethane-1,2-diyl)bis(2-methoxyphenol), THF (40 mL), and CNBr (1.06 g, 10 mmol). The flask was cooled to −20° C. and triethylamine (1.16 mL) was added dropwise. A tan solid immediately precipitated from solution. The mixture was stirred at −20° C. for 10 min and was then removed from the cold bath and allowed to spontaneously warm. After stirring for an additional 30 min, the mixture was filtered on a medium glass-frit and the solid washed with water (3×20 mL) and then air dried to yield 0.71 g of crude product. Evaporation of the filtrate followed by water and ether washes yielded an additional 0.22 g of product for a total of 0.93 g (76%). Recrystallization from hot THF yielded 625 mg of tan needles. $^1$H NMR (DMSO-d$_6$) δ 7.42 (d, 2 H, J=8 Hz), 7.18 (s, 2 H), 6.91 (d, 2 H, J=8 Hz), 3.88 (s, 3 H, OMe), 2.91 (s, 2 H, CH$_2$), Anal. Calcd for $C_{18}H_{16}O_4N_2$: 66.86; H. 4.97. Found: C, 66.67; H 4.96.

Test Sample Preparations.

Monomeric samples were degassed along with a silicone mold at 20° C. above the melting point and 300 torr prior to use, except when sample melting points were higher than 130° C., in which case only the silicone mold was degassed at 95° C. and 30 torr. Sample discs measuring 12 mm in diameter×1-3 mm thick were fabricated by pouring the uncatalyzed monomer into the mold and curing under flowing nitrogen for 1 hr at 150° C. (when permitted by a sufficiently low melting point) followed by 24 hours at 210° C. The temperature ramp rate during cure was 5° C./min. The resultant discs weighed 0.2-0.4 mg.

Physical Analysis.

Differential scanning calorimetry was performed on ~10 mg samples of monomer reserved after de-gassing using a TA Instruments Q200 calorimeter under 50 mL/min. of flowing nitrogen. Samples were heated to 350° C., cooled to 100° C. and re-heated to 350° C., all at 10° C./min. The discs were tested via dynamic thermomechanical analysis (dynamic TMA) with a TA instruments Q400 series analyzer under 50 mL/min of nitrogen flow. The discs were held in place via a 0.2 N mean compressive force the standard ~5 mm diameter flat cylindrical probe while the probe force was modulated at 0.05 Hz over an amplitude of 0.1 N and the temperature was ramped to 350° C. at 10° C./min. These rapid heating rates were needed to minimize post-cure of the samples during testing. The thermal lag for each sample was determined (using temperature limits of 100° C. and 200° C. and used to correct the TMA thermocouple readings (typically about 5° C.) via a temperature cycling procedure described in detail elsewhere.[17] The infrared analysis was performed by Attenuated Total Reflection Fourier Transform infrared (ATR-FTIR) spectroscopy using a single bounce diamond ATR crystal. The instrument used was a Nexus 870 FTIR spectrometer with a liquid N$_2$ cooled cadmium telluride (MCTA) detector. Each spectrum is an average of 28 scans at 4 cm$^{-1}$ resolution.

Analysis by Simultaneous TGA-FTIR.

Thermal gravimetric analysis—Fourier transform infrared (TGA-FTIR) analysis were performed using a Nicolet Nexus 870 FTIR spectrometer interfaced by a heated gas cell and transfer line (held at 150° C.) to a TA instruments Q50 TGA. The FTIR was programmed to acquire a spectrum every 10 seconds integrating 8 scans per spectrum, 256 scan for the background. The detector type was a liquid nitrogen cooled MCTA and the resolution was set at 4 cm⁻. The TGA was set to ramp the temperature at 10° C./min to 200° C./min to 400° C.

Vanillin can be made into a variety of dimer products using chemistries that include but not limited to:

Direct coupling of the aromatic rings through biotic or abiotic oxidants directly with vanillin or derivatives made from vanillin:

Reactions coupling the vanillin rings or compounds derived from vanillin using electrophilic aromatic substitution including reactions with ketones, aldehydes, formaldehyde, fluorinated and perfluorinated ketones, dimethoxymethane, and other bis(chloromethyl)-alkyl derivatives:

Functionalization of the hydroxy groups with reactive chemical groups like cyanate, isocyanate, acrylates, methacrylates, fluorinated vinyl, and other reactive chemical groups capable of undergoing polymerization chemistry know to persons practices in the art of polymers. Resin structure made from biphenyl-vanillin cyanate ester monomer:

Other Bis(aryl) Cyanate Ester Monomers and Model Compounds are shown below:

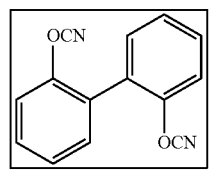

2,2'-dicyanato-1,1'-biphenyl

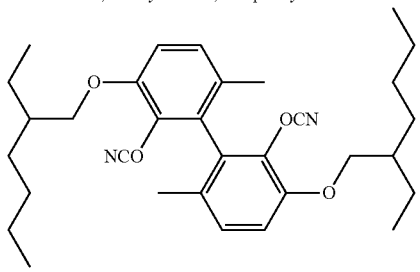

2,2'-dicyanato-3,3'-bis((2-ethylhexyl)oxy)-6,6'-dimethyl-1,1'-biphenyl

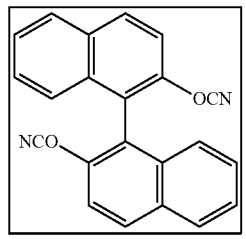

2,2'-dicyanato-1,1'-binaphthalene

Embodiments of the invention generally relate to methods for converting vanillin to bis(cyanate) ester monomers including, treating vanillin with hydrogen in the presence of a metal catalyst to afford 4-methyl-2-methoxyphenol, treating the 4-methyl-2-methoxyphenol under oxidative coupling conditions that induce a coupling of the aromatic rings at the 6-position to afford 6,6-methyl-3,3-dimethoxy-2,2- dihydroxybiphenyl, treating the 6,6-dimethyl-3,3-dimethoxy-2,2-dihydroxybiphenyl with at least one cyanogen halide and base in an organic solvent to create a new biphenyl cyanate ester monomer, and purifying the monomer is achieved by recrystallizing or precipitating from an organic solvent.

Another embodiment of the invention generally relates to methods for converting vanillin to bis(cyanate) ester monomers including, treating vanillin with a reductive coupling agent to form 1,2-bis(4-hydroxy-3-methoxyphenyl)ethene (olefin), treating the 1,2-bis(4-hydroxy-3-methoxyphenyl) ethene with hydrogen and a metal catalyst to hydrogenate the olefin to form 1,2-bis(4-hydroxy-3-methoxyphenyl)ethane, treating the 1,2-bis(4-hydroxy-3-methoxyphenyl)ethane with at least one cyanogen halide and base in an organic solvent to afford 1,2-bis(4-cyanato-3-methoxyphenyl)ethane (monomer), and purifying the monomer is achieved by recrystallization or precipitation from an organic solvent.

Yet another embodiment of the invention generally relates to method of preparing high $T_g$ composite parts from bis (cyanate) ester monomers (resins) including, dispersing the vanillin based bis(cyanate) ester monomers with composite cloth to produce a mixture of cyanate ester monomers, heating the mixture of cyanate ester monomer and the composite cloth to at least above 100 deg C. for a period of about 1-24 hours in a mold, and removing composite cloth component from mold.

Still yet other embodiments of the invention generally relate to methods for converting vanillin to resins and polymers including, treating vanillin with hydrogen in the presence of a metal catalyst to afford 4-methyl-2-methoxyphenol, treating the 4-methyl-2-methoxyphenol under oxidative coupling conditions that induce a coupling of the aromatic rings at the 6-position to afford 6,6-dimethyl-3,3-dimethoxy-2,2-dihydroxybiphenyl, converting the 6,6-dimethyl-3,3-dimethoxy-2,2-dihydroxybiphenol to a resin or polymer by conventional methods, purifying the resin or polymer to be achieved by recrystallization or precipitation.

Embodiments of the invention generally relate to methods for converting vanillin to resins and polymers including, treating vanillin with a reductive coupling agent to form 1,2-bis(4-hydroxy-3-methoxyphenyl)ethene (olefin), treating the 1,2-bis(4-hydroxy-3-methoxyphenyl)ethene with hydrogen and a metal catalyst to hydrogenate the olefin, converting the 1,2-bis(4-hydroxy-3-methoxyphenyl)ethane to a resin or polymer by conventional methods, and purifying the resin or polymer to be achieved by recrystallization or precipitation.

In embodiments, the metal catalyst is selected from the group consisting of nickel, palladium, and platinum used as single metals, mixtures thereof, supported on carbon and other inorganic supports including alumina. In embodiments, the hydrogen pressure is ranging from 1 psig to about 6000 psig. In other embodiments, the hydrogen pressure is 100 psig. In embodiments, the halide is selected from the group consisting of bromide, iodide, and chloride. In embodiments, the oxidative coupling agent is an oxidative enzyme of biological origin. In embodiments, the enzyme is horseradish peroxidase. In embodiments, the oxidative coupling agent used in the chemical reaction is regenerated by electrochemical methods. In embodiments, bis(cyanate) ester monomers produced by the methods above.

In embodiments, the reductive coupling agent is generated by treating titanium halides with magnesium, zinc, or manganese metal. In embodiments, the halide is selected from the group consisting of bromide, chloride, and iodide. In embodiments, the composite cloth is based on silicate glass. In embodiments, the composite cloth is based on graphitic-like carbon or synthetic fibers. In embodiments, the metal catalyst can be selected from group nickel, palladium, and platinum used as single metals, mixtures thereof, or supported on carbon or other inorganic supports including alumina. In embodiments, the pressure is from 1 psig to 6000 psig with 100 psig.

In embodiments, the polymer is selected from the group consisting of polycarbonates, epoxy resins, polyester resins, polysulfones, polyester-styrene, alkylphenolic resins, and polyalylates. In embodiments, the oxidative coupling agent is an oxidative enzyme of biological origin. In embodiments, the polymer or resin includes is selected from the group consisting of polycarbonates, epoxy resins, polyester resins, polysulfones, polyester-styrene, alkylphenolic resins, and polyalylates. In embodiments, the reductive coupling agent generated by treating titanium-halides with magnesium, zinc, or manganese metal.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in the stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for converting vanillin to bis(cyanate) ester monomers, comprising:
    treating vanillin with a reductive coupling agent to form 1,2-bis(4-hydroxy-3-methoxyphenyl)ethene, wherein the reductive coupling agent is generated by treating titanium halides with magnesium, zinc, or manganese metal;
    treating said 1,2-bis(4-hydroxy-3-methoxyphenyl)ethene with hydrogen and a metal catalyst to form 1,2-bis(4-hydroxy-3-methoxyphenyl)ethene;
    treating said 1,2-bis(4-hydroxy-3-methoxyphenyl)ethane with at least one cyanogen halide and base in an organic solvent to form 1,2-bis(4-cyanato-3-methoxyphenyl)ethane; and
    purifying said 1,2-bis(4-cyanato-3-methoxyphenyl)ethane by recrystallization or precipitation from an organic solvent.

2. The method according to claim 1, wherein said cyanogen halide is selected from the group consisting of cyanogen bromide, cyanogen chloride, and cyanogen iodide.

* * * * *